(12) United States Patent
Kobayashi et al.

(10) Patent No.: US 7,443,059 B2
(45) Date of Patent: Oct. 28, 2008

(54) LINEAR ACTUATOR FOR BOTH VIBRATING AND ROLLING MOVEMENT AND ELECTRIC TOOTHBRUSH USING THE SAME

(75) Inventors: Noboru Kobayashi, Hikone (JP); Takahiro Nishinaka, Omihachiman (JP); Kensaku Kanada, Hikone (JP); Hiroaki Shimizu, Hikone (JP); Ryo Motohashi, Hikone (JP); Hidekazu Yabuuchi, Hikone (JP)

(73) Assignee: Matsushita Electric Works, Ltd., Osaka (JP)

(*) Notice: Subject to any disclaimer, the term of this patent is extended or adjusted under 35 U.S.C. 154(b) by 528 days.

(21) Appl. No.: 11/330,204

(22) Filed: Jan. 12, 2006

(65) Prior Publication Data

US 2006/0168745 A1    Aug. 3, 2006

(30) Foreign Application Priority Data

Jan. 19, 2005    (JP)    ............................. 2005-012085

(51) Int. Cl.
    *H02K 41/00*    (2006.01)
(52) U.S. Cl. .......................................... 310/12; 310/36
(58) Field of Classification Search ................... 310/12, 310/15, 17, 36
    See application file for complete search history.

(56) References Cited

U.S. PATENT DOCUMENTS

| | | | |
|---|---|---|---|
| 6,709,162 B2 * | 3/2004 | Muraki et al. ............... | 384/504 |
| 2002/0195884 A1 | 12/2002 | Ichii et al. | |
| 2005/0235438 A1 * | 10/2005 | Motohashi et al. ........... | 15/22.1 |
| 2006/0168745 A1 * | 8/2006 | Kobayashi et al. ........... | 15/22.1 |
| 2007/0011834 A1 * | 1/2007 | Shimizu et al. ............... | 15/22.1 |

FOREIGN PATENT DOCUMENTS

| | | |
|---|---|---|
| EP | 1193844 | 4/2002 |
| JP | 2002-176758 | 6/2002 |
| JP | 3475949 | 9/2003 |
| JP | 2004-254411 | 9/2004 |

(Continued)

OTHER PUBLICATIONS

U.S. Appl. No. 10/557,253 to Shimizu et al., filed Nov. 16, 2005.

(Continued)

*Primary Examiner*—James Harvey
(74) *Attorney, Agent, or Firm*—Greenblum & Bernstein, P.L.C.

(57) ABSTRACT

The linear actuator for both vibrating and rolling movement according to one preferred embodiment of the present invention is comprised of a shaft supported so as to be movable reciprocally in an axis direction and a rotation direction about the axis, a first linear driver including a cylindrical stator having a winding wire thereon and a movable member arranged inside the stator so as to reciprocate the shaft linearly in the axis direction, a second linear driver including a cylindrical stator having a winding wire thereon and a movable member arranged inside the stator so as to reciprocate the shaft rollingly in the rotation direction, one of the movable members being secured on the shaft and another one of the movable members being movable relative to the shaft, and a coordinating member for enabling the shaft and the one of the movable member to move in opposite phase to the another one of the movable member.

9 Claims, 7 Drawing Sheets

FOREIGN PATENT DOCUMENTS

| | | |
|---|---|---|
| JP | 2004-343933 | 12/2004 |
| WO | 2004/102777 | 11/2004 |

OTHER PUBLICATIONS

U.S. Appl. No. 10/557,055 to Shimizu et al., filed Nov. 16, 2005.
U.S. Appl. No. 10/557,252 to Shimizu et al., filed Nov. 16, 2005.
U.S. Appl. No. 11/330,202 to Shimizu et al., filed Jan. 12, 2006.
English language Abstract of JP 2002-176758. Jun. 21, 2002.
An English language abstract of patent family member Japanese Laid-open Patent Publication No. 2002-199689. Jul. 12, 2002.
English language Abstract of JP 2004-343933. Dec. 2, 2004.
English Language Abstract of JP 2004-254411. Sep. 9, 2004.

\* cited by examiner

LINEAR ACTUATOR FOR BOTH VIBRATING AND ROLLING MOVEMENT AND ELECTRIC TOOTHBRUSH USING THE SAME

CROSS REFERENCE TO RELATED APPLICATION

This application claims benefit of priority under 35 U.S.C. § 119 to Japanese Patent Application No. 2005-12085, filed on Jan. 19, 2005, the entire contents of which are incorporated by reference herein.

BACKGROUND OF THE INVENTION

1. Field of the Invention

The present invention relates to a linear actuator for both vibrating and rolling movement, capable of reciprocating in both a linear and a rolling manner, and an electric toothbrush using the same.

2. Description of the Related Art

A linear actuator capable of reciprocating linearly along a given axis and rolling about the axis has been disclosed in Japanese Patent Application Laid-open Publication No. 2004-343933. The linear actuator is composed of a shaft supported so as to reciprocate linearly along an axis thereof and to roll about the axis, a linear driver for causing the shaft to reciprocate linearly along the axis, and a linear driver for causing the shaft to roll about the axis.

The linear driver for linearly reciprocating movement is composed of a vibrating element and a stator. The vibrating element is cylinder-shaped and provided coaxially around a part of the circumference of the shaft. Also, the vibrating element is provided at both ends thereof with cylindrical permanent magnets having different magnetic poles on both ends thereof. The stator of the linear driver for linearly reciprocating movement is cylinder-shaped and arranged coaxially around the vibrating element. Also, this stator has a winding wire therearound.

The linear drive for rollingly reciprocating movement is composed of a rolling member and a stator. The rolling member is composed of a permanent magnet and a yoke and provided coaxially around another part of the shaft. The stator of the linear driver for rollingly reciprocating movement is cylinder-shaped and arranged coaxially around the rolling element. Also, this stator has a winding wire therearound.

In addition, the linear actuator according to the aforementioned publication is provided with a vibration absorbing weight independently from the above movable members in order to absorb unwanted vibration caused by linear reciprocation along the axis. Namely, such unwanted vibration is absorbed by vibrating the vibration absorbing weight in opposite phase to the moving components composed of the shaft and the movable members.

However, since vibration is absorbed by the vibration absorbing weight moving in opposite phase to the movable members, the vibration absorbing weight is indispensable in addition to the movable members, thereby making the electric toothbrush larger and heavier. In addition, due to an increase in size and total weight, more energy is required for causing reciprocating movements, thereby reducing a driving efficiency.

SUMMARY OF THE INVENTION

The present invention has been made in view of the above disadvantages and the objective thereof is a provision of a small, low-cost and efficient linear actuator for both vibrating and rolling movement and an electric toothbrush using the same. Also, the bent arm portion is provided at the end thereof with a blade back portion that extends substantially parallel with the arm when seen from a lateral side, and the blade back portion is provided with the blades.

In order to achieve the objective, one embodiment of the present invention provides a linear actuator for both vibrating and rolling movement, comprising a shaft supported so as to be movable reciprocally in an axis direction and a rotation direction about the axis; a first linear driver (a linear actuator for linearly reciprocating movement) including a cylindrical stator having a winding wire thereon and a movable member arranged inside the stator so as to reciprocate said shaft linearly in the axis direction; a second linear driver (a linear actuator for rollingly reciprocating movement) including a cylindrical stator having a winding wire thereon and a movable member arranged inside the stator so as to reciprocate said shaft rollingly in the rotation direction, one of said movable members being secured on said shaft and another one of said movable members being movable relative to said shaft; and a coordinating member for enabling said shaft and said one of said movable member to move in opposite phase to said another one of said movable member.

According to the embodiment of the present invention, the movable member of the linear actuator for linearly reciprocating movement and the movable member of the linear actuator for rollingly reciprocating movement move so as to offset or reduce vibration caused by each other.

The movable member of the linear actuator for rollingly reciprocating movement is secured on the shaft while the movable member of the linear actuator for linearly reciprocating movement is movable relative to the shaft in one mode, whereas the movable member of the linear actuator for linearly reciprocating movement is secured on the shaft while the movable member of the linear actuator for rollingly reciprocating movement is movable relative to the shaft in another mode.

Preferably, the movable member that is movable relative to the shaft is provided with a weight-adjusting member so as to retain a mass necessary to efficiently offset or reduce the vibration.

In addition, the coordinating member preferably moves both movable members in opposite phase to each other in the rotation direction of the shaft so as to offset or reduce vibration occurring in the direction.

As the coordinating member, a spring member that constitutes a spring oscillation system along with the movable members is preferably used. This allows for a good use of resonance, thereby enabling to output high power.

The movable member movable relative to the shaft is preferably provided with a weight-adjusting member that is cylinder-shaped and arranged so as to surround the spring member, thereby reducing the radial dimension of the linear actuator.

The movable member movable relative to the shaft is supported preferably by use of the bearing attached on the shaft or the stator, thereby maintaining a predetermined magnetic gap between the movable member and the stator.

The electric toothbrush according to the present invention utilizes the above linear actuator for both vibrating and rolling movement as a driving source and includes the brush driven by the shaft of the linear actuator, thereby providing a lightweight electric toothbrush with reduced vibration.

According to the present invention, since the movable member of the linear driver for linearly reciprocating movement and the movable member of the linear driver for rollingly reciprocating movement can offset vibration caused by each other, the vibration absorbing weight is not necessary as an additional member for absorbing vibration, thereby realizing a down-sized and lightweight linear actuator. In addition, such a linear actuator can save driving energy, thereby providing an advantage of downsizing.

DESCRIPTION OF THE PREFERRED EMBODIMENTS

Figure 1:
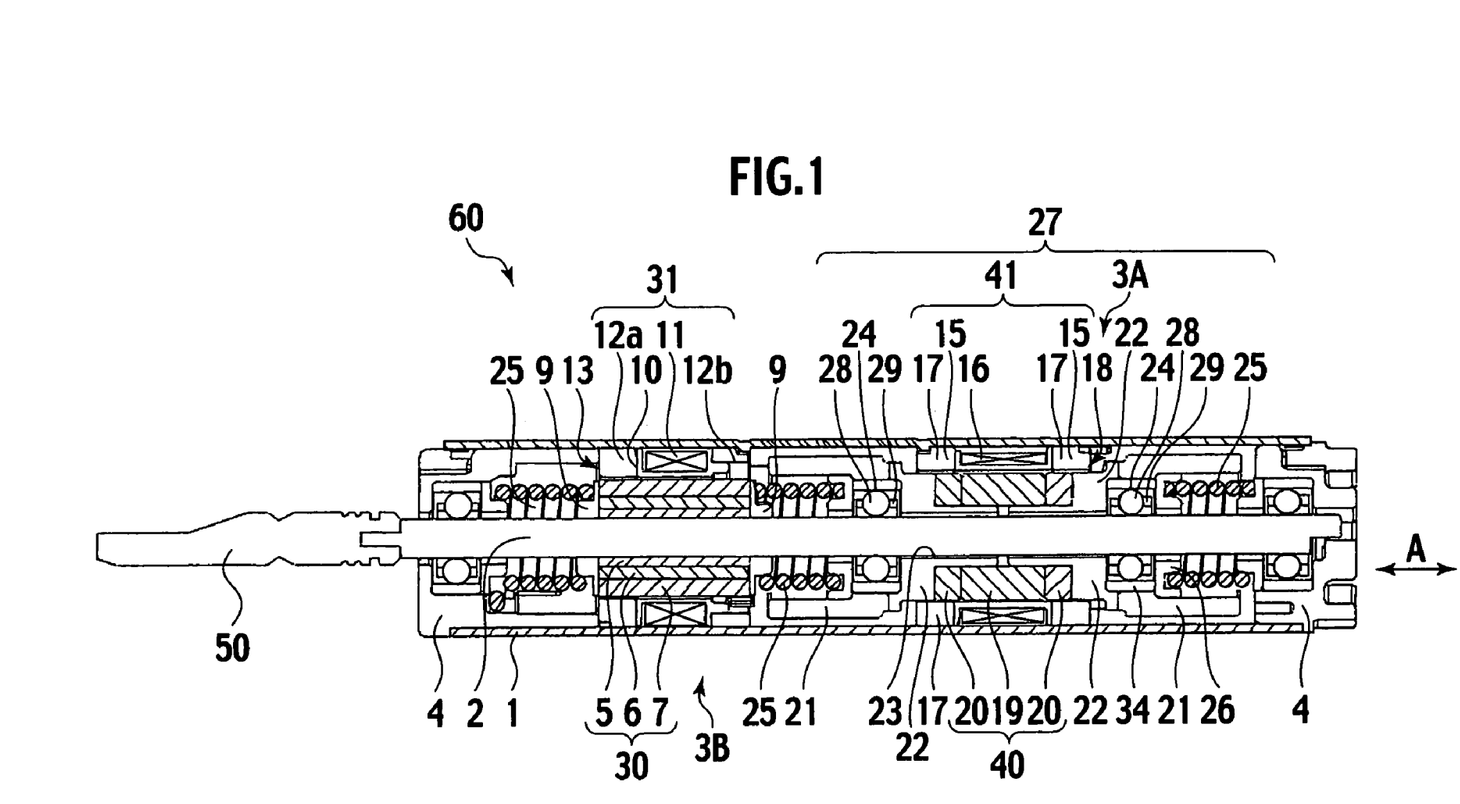
FIG. 1 is a cross-sectional view of one preferred embodiment according to the present invention.
Figure 2:
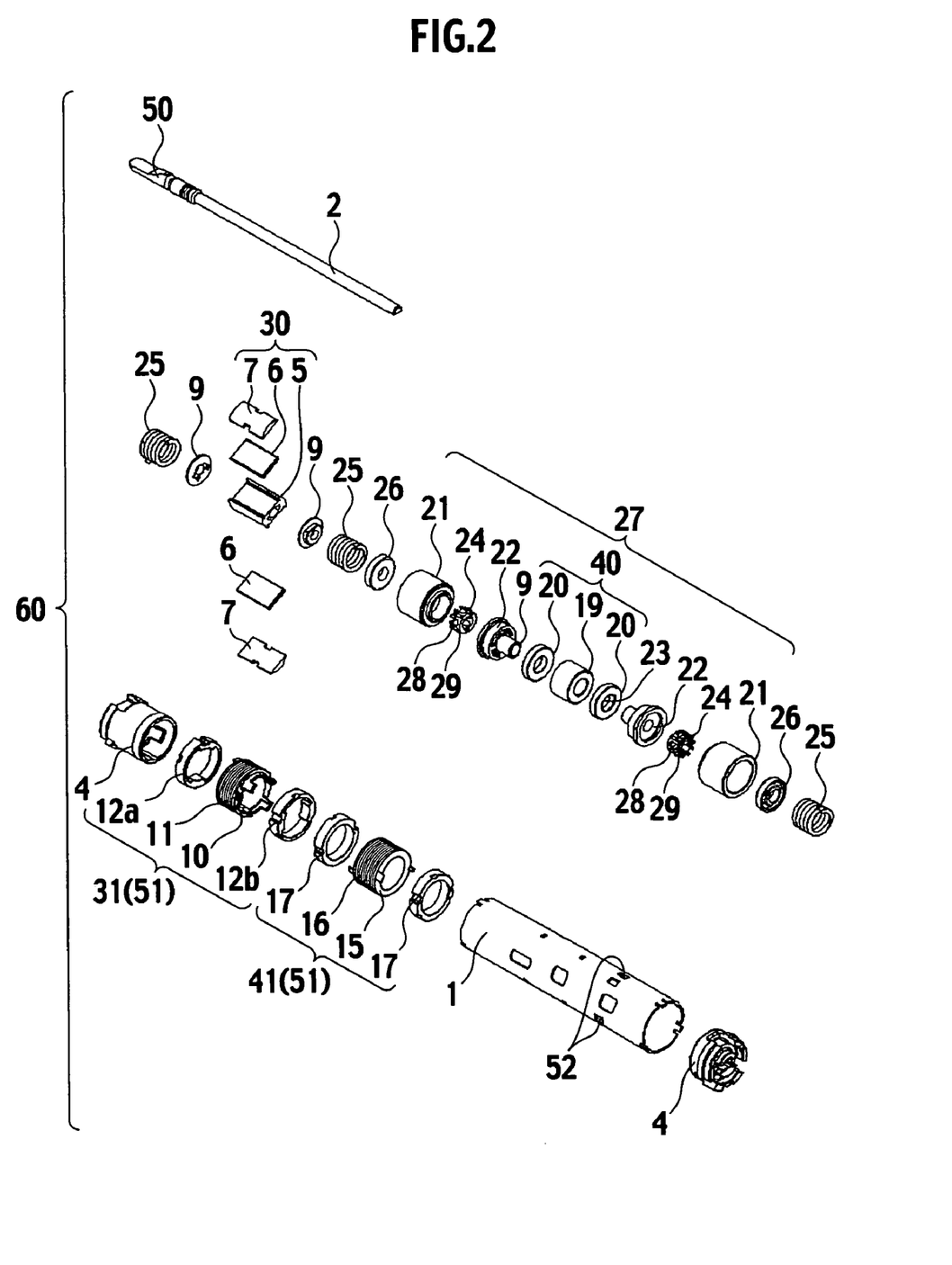
FIG. 2 is an exploded perspective view corresponding to FIG. 1.

Referring to accompanying drawings, preferred embodiments of the present invention will be described in detail. FIGS. 1 and 2 illustrate a linear actuator 60 for both vibrating and rolling movement as a first embodiment of the present invention. As shown, the linear actuator 60 for both vibrating and rolling movement is composed of a linear driver 3A for linearly reciprocating a shaft 2 in an axis direction A and a linear driver 3B for rollingly reciprocating the shaft 2 in a rotation direction B, the drivers 3A, 3B being provided inside a cylindrical shield case 1.

The shaft 2 is supported at both ends thereof by bearings 4, 4 so as to be able to linearly reciprocate in the axis direction A and roll in the rotation direction B. The bearings 4, 4 are attached respectively in both ends of the shield case 1. At the tip of the shaft 2 is provided a transmission member 50 that transmits a driving force to an exterior member.

The linear driver 3B for rollingly reciprocating movement is composed of a rolling member 30 secured on the shaft 2, and a stator 31 arranged in a position corresponding to the rolling member 30 inside the shield case 1. The rolling member 30 is composed of a cylindrical rolling yoke 5 made of a magnetic material, a plate-shaped permanent magnet 6 and a semicircular rolling yoke 7 made of a magnetic material. The cylindrical rolling yoke 5 of the rolling member 30 is secured on the shaft 2 by adhering, press-fitting, welding, or screwing.

On the circumference of the cylindrical rolling yoke 5 are provided two flat surfaces so as to form two grooves 8, 8 opposing parallel with each other. The plate-shaped permanent magnet 6 is fitted into each groove 8 and the semicircular rolling yoke 7 is attached on top of the plate-shaped permanent magnet 6. With this configuration, a circular arc of the semicircular rolling yoke 7 substantially creates a circle along with a circular arc of the cylindrical rolling yoke 5, as shown in FIG. 3B.

The inner surface and the outer surface of the plate-shaped permanent magnet 6 have different magnetic poles, wherein the inner surface is a surface facing inward relative to a direction C orthogonal to the axis direction A of the shaft 2 whereas the outer surface is a surface facing outward. Namely, when the outer surfaces of the two permanent magnets 6 are North Pole, the inner surfaces are all South Pole, and the opposite is true.

On the other hand, the stator 31 constituting the linear driver 3B for rollingly reciprocating movement is composed of a coil member made by winding a wire 11 (a winding wire 11, hereinafter) around a coil bobbin 10 and cylindrical stationary parts 12a, 12b arranged on both ends of the coil bobbin 10 of the coil member, so as to take a shape of cylinder as a whole. As illustrated in FIG. 3B, the stator 31 is provided inside the shield case 1 in such a way that the inner surface thereof opposes the outer surface of the rolling member 30 leaving a predetermined magnetic gap 13 therebetween.

Figure 3A:
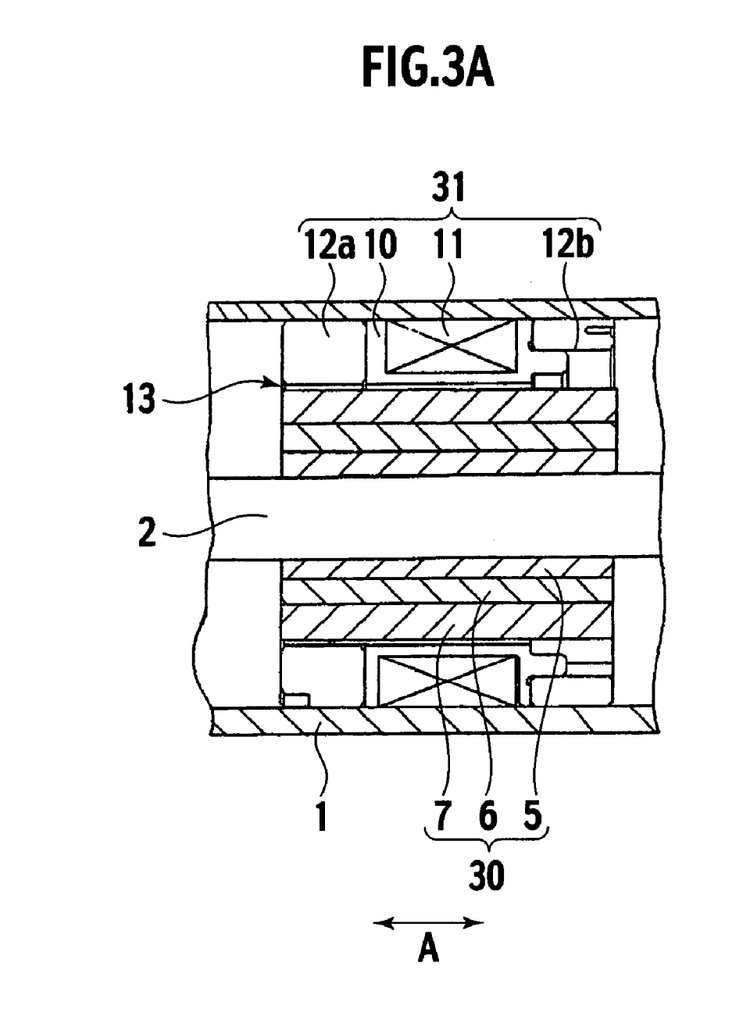
FIG. 3A is a vertical cross-sectional view of a linear driver for rollingly reciprocating movement.
Figure 3B:
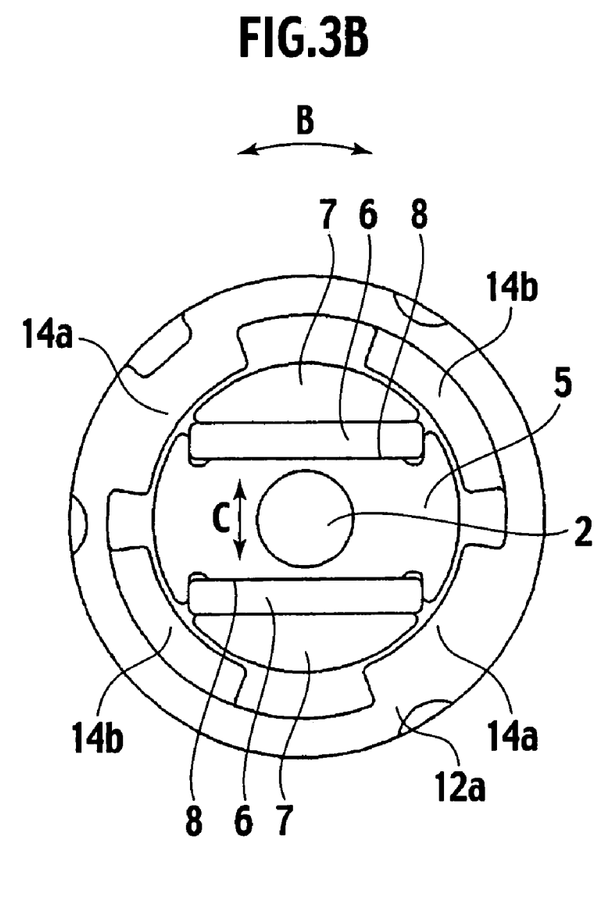
FIG. 3B is a horizontal cross-sectional view of the linear driver for rollingly reciprocating movement.

On the inner surface of the cylindrical stationary part 12a, two magnetic pole members 14a, 14a are provided so as to oppose the rolling member 30 (FIG. 3B). Similarly, two magnetic pole members 14b opposing the rolling member 30 are provided on the inner surface of the cylindrical stationary part 12b. The number of the magnetic pole members 14a, 14b is the same as that of the permanent magnets 6 of the rolling member 30 in this embodiment. In addition, the magnetic pole members 14a in the cylindrical stationary part 12a alternate in the angular direction with the magnetic pole members 14b in the cylindrical stationary part 12b (FIG. 3B), as seen from the axis direction A.

In the liner driver 3B for rollingly reciprocating movement configured in such a way, when a direct current flows through the winding wire 11 in one direction, the rolling member 30 rotates in one rotation direction of B, while when the current flows in the opposite direction, the rolling member 30 rotates in the opposite direction accordingly. Therefore, when an alternating current flows through the winding coil 11, the rolling member 30 can roll reciprocally in the rotation direction B.

Next, the linear driver 3A for linearly reciprocating movement is composed of a vibrating member 40 and a stator 41. The stator 41 is composed of a coil member made by winding a wire 16 (a winding wire, hereinafter) around a coil bobbin 15 and cylindrical stationary parts 17, 17 arranged on both sides of the coil bobbin 15 of the coil member, so as to take a shape of cylinder as a whole. The stator 41 is provided inside the shield case 1 so as to surround coaxially the vibrating member 40 leaving a predetermined magnetic gap 18 between the inner surface of the stator 41 and the outer surface of the vibrating member 40.

The vibrating member 40 is composed of a cylindrical yoke 19 made of a magnetic material and cylindrical permanent magnets 20, 20 provided on both ends of the yoke 19. On both ends of the vibrating member 40 is provided a weight 21 for adjusting weight by means of a connection member 22. The permanent magnets 20, 20 are positioned in such a way that the outer surface thereof opposes the inner surface of the stationary parts 17, 17 of the stator 41. Both ends along the direction A of each permanent magnet 20 have different magnetic poles and the outer ends, which do not face the yoke 19, of the permanent magnets 20, 20 have the same magnetic pole.

The vibrating member 40 is cylinder-shaped having a through-hole 23 through which the shaft 2 penetrates. The vibrating member 40 is movably attached on the shaft 2 by means of a pair of bearings 24, 24. Due to the bearings 24, 24, the vibration member 40 and the shaft 2 are able to independently move in the axis direction A and the rotation direction B.

Between a spring support 26 at one end of the vibrating member 40 and one end of the shield case 1, there is disposed a spring member 25 made into a helical compression spring. Similarly, between a spring support 21 at the other end of the vibrating member 40 and a spring support 9 at one end of the rolling member 30, there is disposed a spring member 25 made into a helical compression spring. Moreover, between a spring support 9 at the other end of the rolling member 30 and the other end of the shield case 1, there is disposed another spring member 25 made into a helical compression spring. With these configurations, the shaft 2 plus the rolling member 30 secured on the shaft 2 and the vibrating member 40 constitute a spring oscillation system in the axis direction.

The permanent magnets 20, 20 of the vibrating member 40 and the winding coil 16 of the stator 41 create a magnetic circuit, which thus enables the vibrating member 40 to linearly reciprocate along the axis direction A. Namely, when a direct current flows through the winding wire 16 of the stator 41 in one direction, the vibrating member 40 moves in one direction along the axis direction A, whereas when the direct current flows in the other direction the vibrating member 40 moves in the opposite direction. Therefore, the vibrating member 40 linearly reciprocates along the axis direction A by applying an alternating current to the winding coil 16.

Such movement of the vibrating member 40 then causes the rolling member 30 and the shaft 2 to move along the axis direction A. Here, the spring oscillation system composed of three spring members 25, the shaft 2, the rolling member 30, and the vibrating member 40 has its own resonance frequency determined by a mass of the shaft 2 and the members 30, 40 and a spring constant of the spring members 25. When the frequency of the alternating current is set as about this resonance frequency, the rolling member 30 plus the shaft 2 and the vibrating member 40 have to move under a resonance condition. As a result, the rolling member 30 and the shaft 2 lead to linearly reciprocate in opposite phase to the vibrating member 40. Namely, the spring members 25 constitute a coordinating member that enables the shaft 2 and the rolling member 30 secured thereon to move in opposite phase to the vibrating member 40.

By the way, the spring members 25 also serve as a member for constituting the spring oscillation system in terms of the rotation direction.

As stated above, in the linear actuator according to this embodiment, the linear driver 3A for linearly reciprocating movement and the linear driver 3B for rollingly reciprocating movement operate concurrently, thereby enabling the linearly reciprocating movement in the axis direction A and the rollingly reciprocating movement in the rotation direction B. In addition, the rolling member 30 and the shaft 2 reciprocate in opposite phase to the vibrating member 40, thereby reducing unwanted vibration caused by linear reciprocating movement of the vibrating member 40 due to the opposite phase movement thereof. Namely, it is understood as if the vibrating member 40 equipped with the weights 21, 21 served for the shaft 2 as the vibration absorbing weight in the related art.

Moreover, the vibrating member 40 rollingly reciprocates in substantially the opposite phase to the rolling member 30 and the shaft 2 that reciprocates linearly in the rotation direction B, thereby reducing unwanted vibration caused by the linearly reciprocating movement.

Furthermore, since the reciprocating movements in both the axis direction A and the rotation direction B take place under a resonance condition as stated above and additional vibration absorbing weights for reducing vibration are unnecessary, the moving parts as a whole can be lightweight, thereby producing high output power from rather low energy input. In addition, the vibrating member 40 including the weights 21, 21 and the shaft 2 are both disposed coaxially, thereby making the linear actuator according the this embodiment further small and lightweight.

By the way, the vibrating member 40 is equipped with the weights 21 as stated above in order to counter a mass of the rolling member 30 and the shaft 2 (and a driven member connected to the shaft by use of the transmission member 50). The reason why the weight 21 is cylindrical and arranged so as to surround the spring member 25 is to shorten the dimension of the actuator along the axis.

Furthermore, since the rolling member 30 is secured on the shaft 2 and the vibrating member 40 is provided with the weights 21, 21, the rollingly reciprocating movement of the rolling member 30 is transferred directly to the shaft 2, thereby elevating the output power produced by the shaft 2 moving in the rotation direction.

Figure 4:
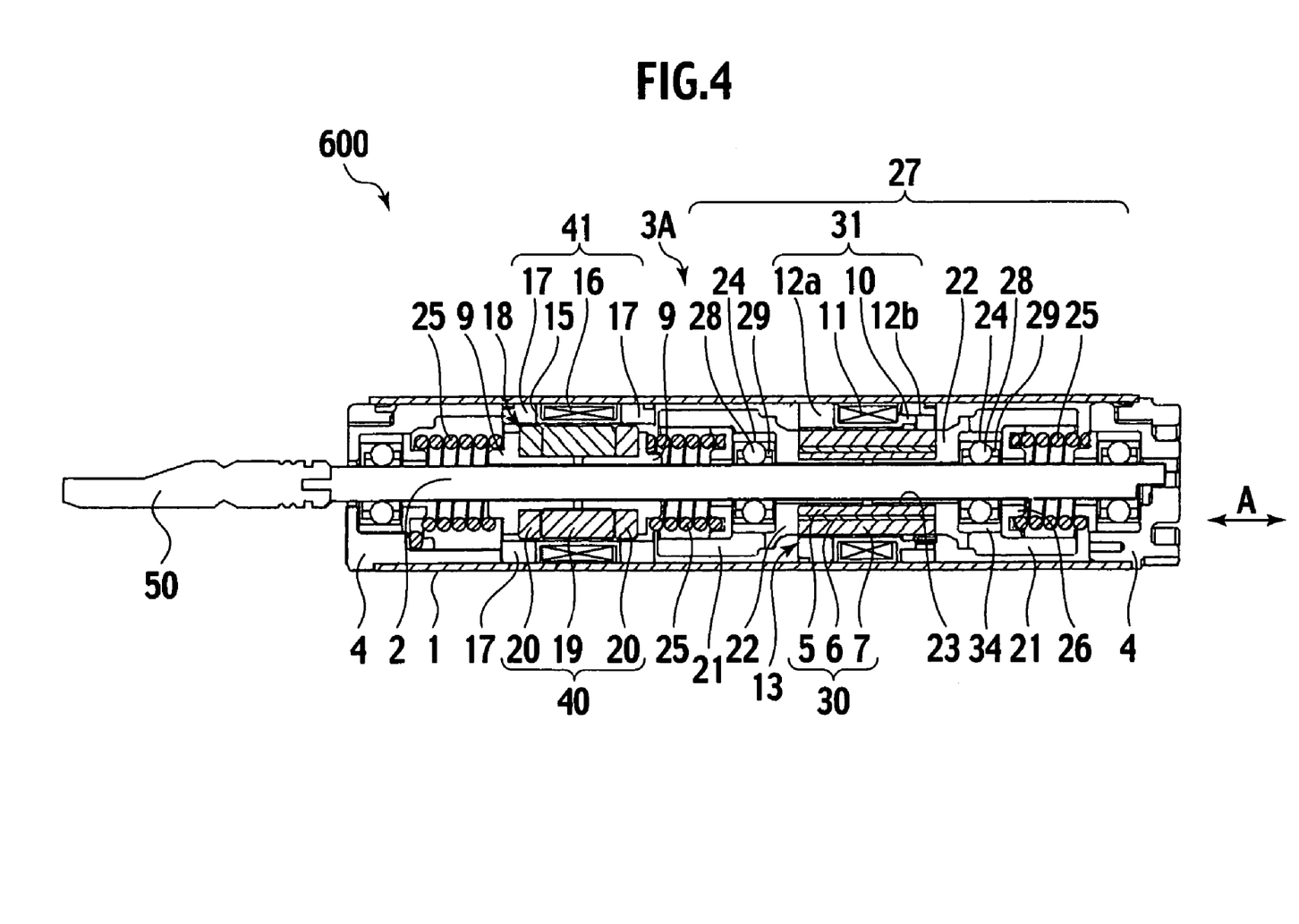
FIG. 4 is a cross-sectional view of another preferred embodiment according to the present invention.

FIG. 4 illustrates another embodiment. This embodiment is different from the aforementioned embodiment in that the linear driver 3A for linearly reciprocating movement and the linear driver 3B for rollingly reciprocating movement change their positions; the vibrating member 40 is secured on the shaft 2; and the rolling member 30 equipped with the weights 21, 21 is supported with the shaft 2 by means of the bearings 24, 24 so that the rolling member 30 is movable in both the axis direction and the rotation direction relative to the shaft 2. In this configuration, the linearly reciprocating movement along the axis direction by the vibrating member 40 is transferred directly to the shaft 2, thereby elevating the output power produced by the shaft 2 moving in the axis direction.

By the way, in the previous embodiments, the vibrating member 40 or the rolling member 30 is supported with the shaft by means of the bearing 24 so as to be movable relative to the shaft 2. Since the bearing 24 is arranged away from the rolling member 30 and not disposed between the inner surface of the stator 41 and the shaft 2, the linear actuator 60 can be downsized in its radial direction. However, this does not necessarily limit the present invention. Namely, the bearing 24 may be disposed between the vibrating member 40 (the rolling member 30) and the stator 41 (stator 31) or between the vibrating member 40 (the rolling member 30) and the shield case 1.

In addition, the bearing 24 that enables the weight 21 secured on the rolling member 30 (or the vibrating member 40) to be movable relative to the shaft 2 serves as a part of the weights 21, 21, thereby making the linear actuator lightweight as a whole. By the way, the bearing 24 is exemplified as a ball bearing composed of steel balls 28, a supporting member 29 for supporting the balls 28, and a receiving member 34 for receiving the balls by the inner surface thereof in the above embodiments. However, the bearing 24 may be a slide bearing provided on the inner surface of the weight 21. In this case, the outer surface of the weight 21 is provided with a slide bearing that then may contact with the stator 41 (the stator 31) or the shield case 1.

Figure 5A:
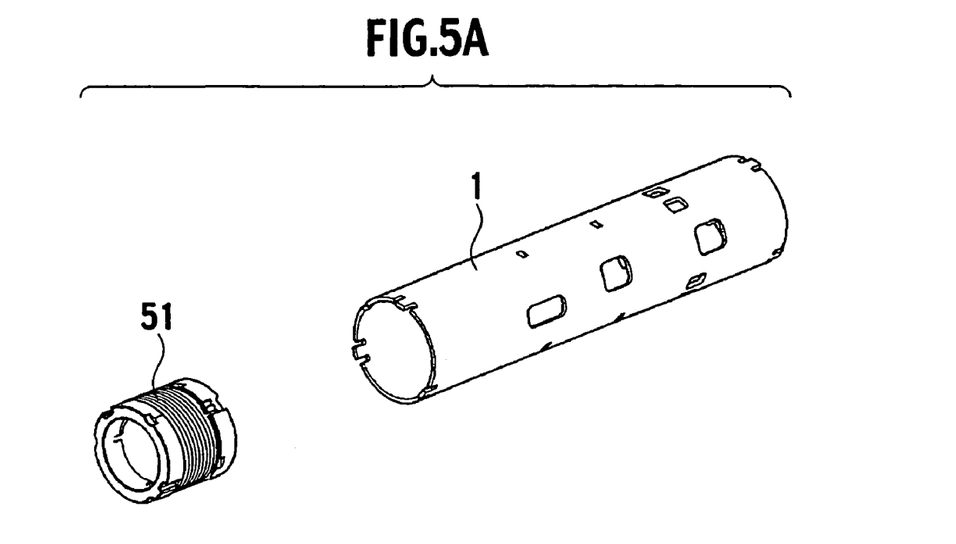
FIGS. 5A and 5B are respectively a perspective and a cross-sectional view of a shield case and a stator.
Figure 5B:
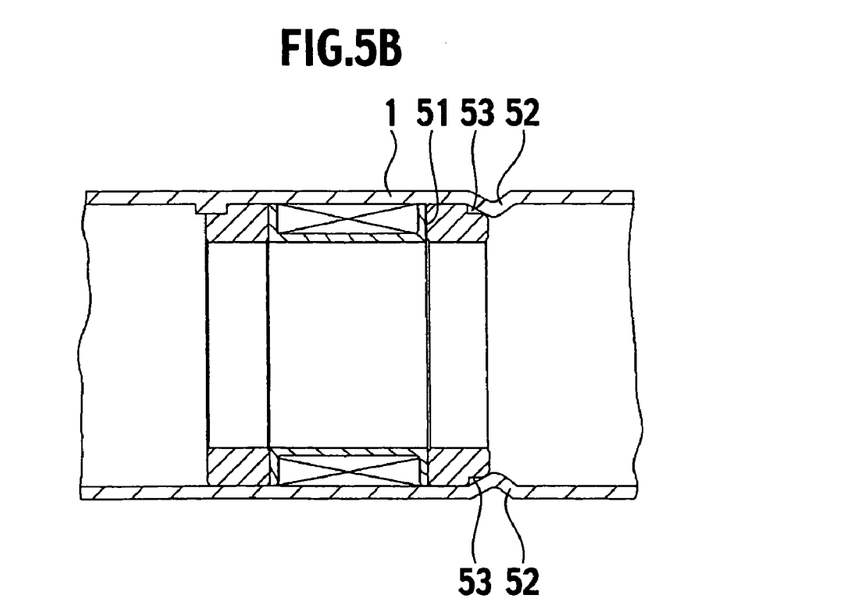

FIGS. 5A and 5B are an example of a stator 51 as an alternative of the aforementioned stators, illustrating how the stator 51 is secured. As illustrated, the stator 51 is inserted into the shield case 1 to be placed at a predetermined position and a caulking portion 52 of the shield case 1 is deformed so that the stator 51 is fitted with the deformed caulking portion 52 and thereby secured in the inside of the shield case 1. At the same time, the calking portion 52 can be fitted into a step 53 (or a notch) made in or on the outer surface of the stator 51, thereby securing the stator 51 in the rotation direction B as well as the axis direction A. As a result, the stator 51 is firmly but easily secured. By the way, the stator 51 may be secured on the shield case 1 by adhering or welding.

Figure 6A:
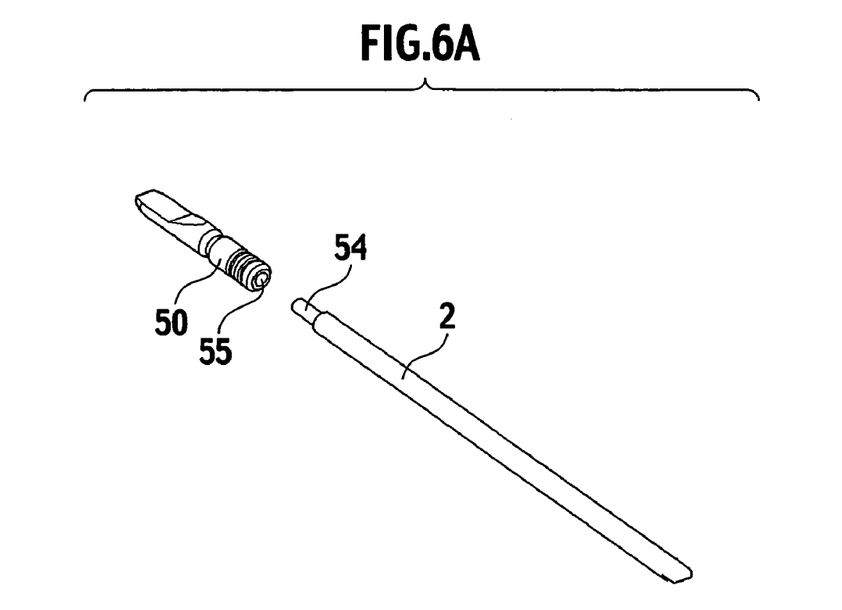
FIGS. 6A and 6B are respectively a perspective and a cross-sectional view of a shaft and a transfer member.
Figure 6B:
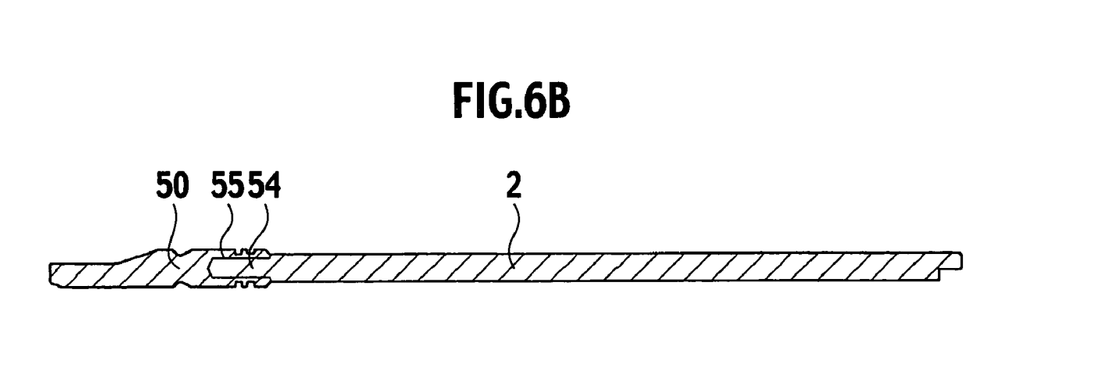

FIGS. 6A and 6B illustrate that a diameter of a tip portion 54 of the shaft 2 is reduced compared the other portion thereof so as to be press-fitted into a hole portion 55 of a transfer member 50 for transferring output power produced by the shaft 2. With this configuration, since the shaft 2 can have a different diameter from the transfer member 50 into which the shaft 2 is fitted, the diameter of the transfer member 50 can be arbitrarily set regardless of that of the shaft 2 and the diameter of the shaft 2 can be reduced irrespective of that of the transfer member 50, thereby down-sizing the linear actuator 60. In addition, this configuration makes it possible to prevent a transfer loss caused when the transfer member 50 slips against the shaft 2 moving in the axis direction A or the rotation direction B. The transfer member 50 may be secured on the shaft by adhering or both press-fitting and adhering.

Figure 7:
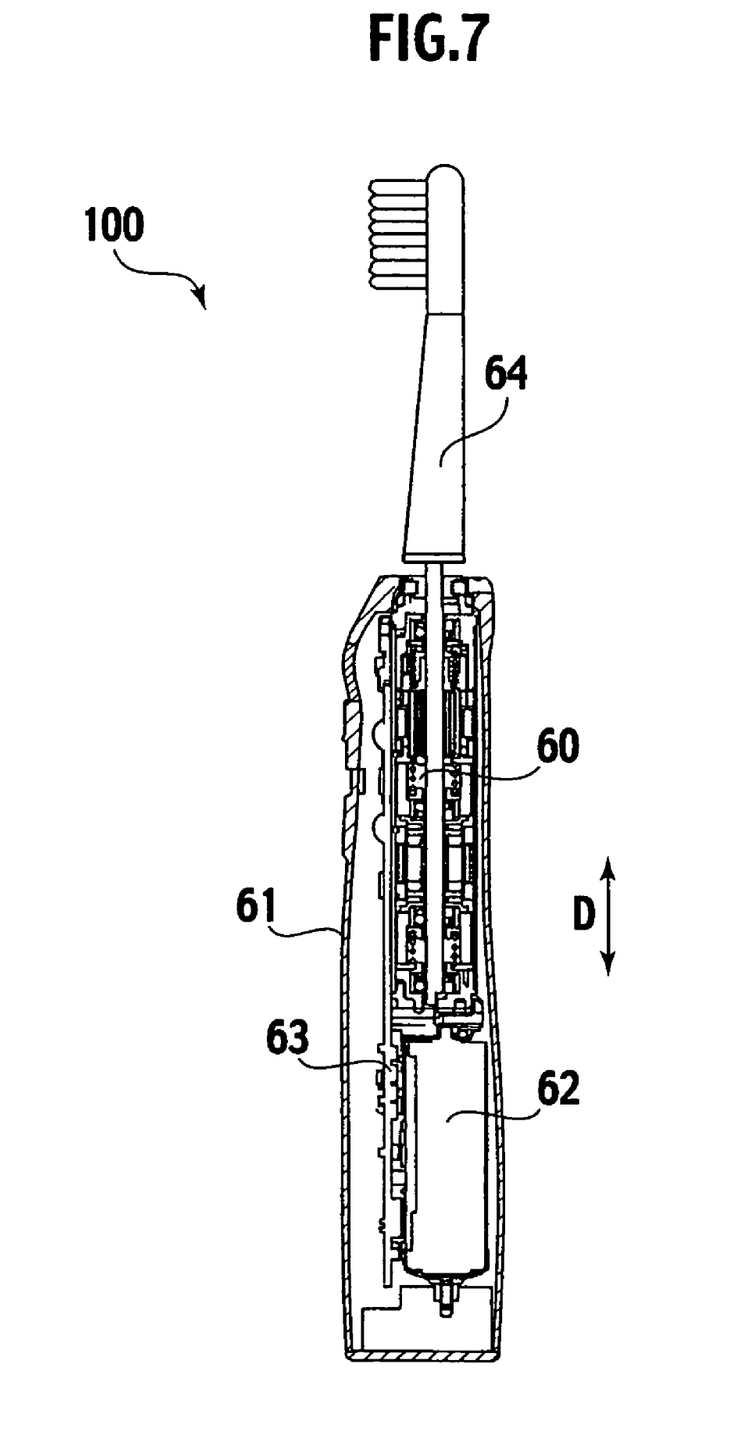
FIG. 7 is a cross-sectional view of one preferred embodiment of an electric toothbrush according to the present invention.

The linear actuator according to the above embodiments of the present invention is applicable as various kinds of drive sources. For example, the linear actuator is applied to an electric toothbrush 100 as illustrated in FIG. 7. As illustrated, the electric toothbrush 100 is composed of a substantially cylindrical housing 61 in which the linear actuator 60 (600) having the same configuration as ones according to the above embodiments and a battery 62 are arranged side by side in a longitudinal direction of the housing 61, a brush 64 attached on the shaft 2 that protrudes from one end of the housing 61 in the longitudinal direction. Also, the electric toothbrush 100 includes a control circuit portion 63 that serves to produce an alternating current from the battery 62, the alternating current having a frequency substantially the same as the resonance frequency of the spring oscillation system in the linear actuator.

In the electric toothbrush 100, the brush 64 can move in both an axis direction and a rotation direction driven by the linear actuator 60, thereby ensuring an effective and efficient brushing of tooth. In addition, since the linear actuator 60 for both vibrating and rolling movement is capable of preventing unwanted vibration, constructed lightweight so as to produce high output power and compact, the electric toothbrush 100 provides comfortable use.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A linear actuator for both vibrating and rolling movement, comprising:
   a shaft supported so as to be movable reciprocally in an axis direction and a rotation direction about the axis,
   a first linear driver including a cylindrical stator having a winding wire thereon and a movable member arranged inside the stator so as to reciprocate said shaft linearly in the axis direction,
   a second linear driver including a cylindrical stator having a winding wire thereon and a movable member arranged inside the stator so as to reciprocate said shaft rollingly in the rotation direction, one of said movable members being secured on said shaft and another one of said movable members being movable relative to said shaft, and
   a coordinating member for enabling said shaft and said one of said movable member to move in opposite phase to said another one of said movable member.

2. A linear actuator for both vibrating and rolling movement as recited in claim 1, wherein said movable member included in said second linear driver is secured on said shaft, and wherein said movable member included in said first linear driver is movable relative to said shaft.

3. A linear actuator for both vibrating and rolling movement as recited in claim 1, wherein said movable member included in said first linear driver is secured on said shaft, and wherein said movable member included in said second linear driver is movable relative to said shaft.

4. A linear actuator for both vibrating and rolling movement as recited in claim 1, further comprising a weight-adjusting member provided on said movable member being movable relative to said shaft.

5. A linear actuator for both vibrating and rolling movement as recited in claim 1, wherein said coordinating member enables said shaft and said movable member secured thereon to move in opposite phase to said movable member being movable relative to said shaft in the rotation direction as well as the axis direction.

6. A linear actuator for both vibrating and rolling movement as recited in claim 1, wherein said coordinating member is a spring member constituting a spring oscillation system along with said movable members.

7. A linear actuator for both vibrating and rolling movement as recited in claim 6, wherein said movable member movable relative to said shaft is provided with a weight adjusting member that is cylinder-shaped and arranged to surround said spring member.

8. A linear actuator for both vibrating and rolling movement as recited in claim 1, wherein said movable member movable relative to said shaft is supported with said shaft or said stator by means of a bearing.

9. An electric toothbrush comprising a linear actuator for both vibrating and rolling movement as recited in claim 1 as a driving source and a toothbrush driven by said shaft of said linear actuator.

* * * * *